United States Patent [19]

Seney

[11] Patent Number: 4,869,668
[45] Date of Patent: Sep. 26, 1989

[54] DENTAL BUR COOLING AND CONTROL SYSTEMS

[76] Inventor: John S. Seney, P.O. Box 152, Sugarloaf Key, Fla. 33044

[21] Appl. No.: 193,043

[22] Filed: May 12, 1988

[51] Int. Cl.[4] .......................... A61C 1/10; A61C 1/12
[52] U.S. Cl. ........................................................ 433/85
[58] Field of Search ................................... 433/84, 85

[56] References Cited

U.S. PATENT DOCUMENTS 3,313,025  4/1967  Hertz .................................... 433/28
3,762,052  10/1973  Melde .................................. 433/165

Primary Examiner—Robert Peshock
Attorney, Agent, or Firm—C. Hercus Just

[57] ABSTRACT

An air-turbine type dental handpiece in which the handle has separate passages for air and water under pressure respectively to drive the turbine to rotate a bur and furnish cooling water to the bur which has an axial passage entirely therethrough to direct the cooling water where the cutting end of the bur contacts tooth material for producing a dental preparation to receive filling material and the like. The head of the handpiece has a chamber within which the turbine and bearings are mounted and also includes a rotary coupling to direct cooling water to the inner end of the axial passage of said bur and prevent escape of the cooling water to the interior of the chamber for the turbine and bearings. Control mechanism to furnish and regulate the pressure of air and water to the handpiece also comprises part of the invention.

20 Claims, 3 Drawing Sheets

DENTAL BUR COOLING AND CONTROL SYSTEMS

BACKGROUND OF THE INVENTION

The preparation of cavities for acceptance of filling material is normally one of the very painful experiences encountered by a patient being subjected to the practice of dentistry. Attempts have previously been made to cool a tooth in which such a preparation is being undertaken by means of a dental assistant spraying water upon the operation, as well as many types of dental handpieces having water jets which operate to direct a stream of water at the area of the tooth where drilling is taking place. None of these systems actually direct cooling fluid such as water into the actual cavity where the cutting is taking place by the bur of the handpiece. Many modern handpieces also operate at very high speeds, as much as 400,000 rpm. Handpieces operating at such speeds require much less pressure than those operating at slower speeds, such as when they are driven by belts and the like.

It has been found by accurate scientific instruments that handpieces operating as such high speeds as mentioned above, involve problems with respect to generating heat in the tooth where the preparation is being formed. Laboratory measurements show a temperature at the bur-tooth interface of 450 degrees F. with a bur pressure of 32 grams at a bur speed of 170,000 rpm, after a running time of 30 seconds. The pulp section of a tooth contains nerves, blood vessels and lymph-carrying vessels, which are destroyed by high temperatures. Fillings placed over such damage can result in infection and abscesses. To alleviate this situation, cooling water jets are built into handpieces with their sprays directed at the cutting bur tip. However, laboratory tests show that little or no water contacts the bur tip per se because of turbulant air surrounding the same. It has been found that a minimum water flow rate of 16 cc/minute is necessary to form a stream with force enough to reach the bur tip area in a commercial 4-hole handpiece. This quantity of water floods the operating area, fogs the dental mirror, and reduces the view of the operating site. Contaminated water mist and sprays exit from the patient's mouth and settles on persons in the general area, creating a serious health hazard, especially when diseases such as AIDS and hepatitus may be present. It has been found that when the bur cuts below the outer surface of the tooth, cooling water entering that area is blocked by the projecting surfaces of the tooth and uncontrolled heating results.

Attempts have previously been made to direct water to the tip of a rotating bur by providing dental burs which have longitudinal passages extending entirely through the bur from one end to the other, but the problems mainly resulting from the use of such burs in dental handpieces resides in difficulties encountered when endeavoring to restrict cooling liquid, such as water, solely through the longitudinal opening in the bur, while in most instances, some of the cooling liquid enters the interior of the head in the vicinity of the turbine, under which circumstances, the lubricant normally required by the bearings of so-called air rotor handpieces is flushed from the bearings or at least diluted by such water. It is the principal object of the present invention to provide a dental handpiece which includes means to direct cooling liquid, such as water, through a bur which is provided with a longitudinal passage between opposite ends and discharge the water from the outer end of the bur directly to the interface between the bur and the tooth and improved means are included which are highly adequate to prevent the cooling liquid from reaching and/or admixing with air turbines and the bearings therefor, details of which are set forth below.

To illustrate the present state of the art in which dental handpieces are provided with burs having axial passages between opposite ends of the bur, and means to direct cooling liquid thereto or therethrough, the following patents are cited as representative of the current state of the art on this subject:

U.S. Pat. No. 2,777,702 - Rodal, Jan. 15, 1957
U.S. Pat. No. 2,799,934 - Kern, July 23, 1957
U.S. Pat. No. 3,624,905 - Barsby, Dec. 7, 1971
U.S. Pat. No. 3,762,052 - Melde (1), Oct. 2, 1973
U.S. Pat. No. 3,871,097 - Melde (2), Mar. 18, 1975
U.S. Pat. No. 4,021,920 - Kirschner et al, May 10, 1977

SUMMARY OF THE INVENTION

It is the principal object of the present invention to provide a dental handpiece for use with a dental bur in which a longitudinal passage extends therethrough between opposite ends thereof, the head of the handpiece being connected to a handle extending therefrom and provided with longitudinal passages therein for cooling liquid, flushing liquid and air to drive the turbine within the head of the handpiece, the principal feature of the present invention comprising a rotary liquid transmission coupling mounted within the upper portion of the head of the handpiece and extending between the passage in the handle for cooling liquid and the upper end of the shaft of the turbine, said coupling including sealing means to prevent the leakage or migration of cooling liquid into the interior of the head in which the turbine, and especially the bearings therefor, are enclosed, whereby the normal lubricant for the bearings is not diluted or otherwise affected.

Another object of the invention is to position said rotary transmission coupling in the upper end of the head of the handpiece and it includes a thin flexible diaphragm sealed at its edges between a relatively flat space in the uppermost portion of the head to receive cooling liquid and results in pressure against one surface of said diaphragm, the opposite face of the diaphragm comprising a closure for a circular space in which the innermost end of the shaft of the turbine is located and said innermost end including a rotary seal member which engages the opposite surface of the diaphragm from that which is adjacent said thin space which accommodates cooling liquid, said annular space communicating with a bypass for part of the driving air for the turbine, whereby air exerts limited pressure against one face of the diaphragm while cooling liquid exerts pressure against the opposite face and the pressure and volume of the air and cooling liquid are regulated so that the rotary seal will always contact the diaphragm and said diaphragm and rotary seal have openings which are coaxial with the axial passage for cooling liquid in the bur and due to such regulation of pressure and volume referred to, a liquid seal is maintained between said rotary seal and diaphragm.

One further object of the invention is to form said diaphragm preferably from a self-lubricating plastic, such as one sold under the trademark "MYLAR", and the rotary seal is formed from solid carbon, whereby minimum friction occurs between the relatively rotating surfaces of the rotary seal and diaphragm, the principal purpose of the air exerting pressure against one surface of the diaphragm is to prevent undue friction between the diaphragm and rotary seal, especially at the start-up of the turbine and until cooling liquid can be exerted against the opposite surface of the diaphragm and discharge through the coaxial opening in the diaphragm and rotary seal and thereafter pass through the bur to the outermost end thereof.

A still further object of the invention is to provide control means for the delivery of cooling liquid and air to the head of the handpiece, said substances being conducted in separate conduits respectively including filters, pressure regulators, electric solenoid valves which are respectively connected to sources of current and include lines within which control switches are provided in conjunction with a foot-operated switch, the handle of the handpiece also including a still further longitudinal passage through which flushing water passes from a source through another control switch of electric solenoid nature, the flushing liquid being directed to an exterior nozzle adjacent the head of the handpiece and extending toward the outer end of the bur for purposes of flushing debris from a cavity preparation operation. In addition to the cooling liquid discharging through the tip of the bur at the innerface between the bur and tooth surface to cool the area being cut by the bur and thus afford relative comfort to a patient, the respective control switches in the lines for the cooling and flushing liquids being operable in conjunction with the foot-operated switch to selectively discharge driving air to the turbine, cooling liquid only to the tip of the bur, flushing liquid only to the flushing jet, both cooling liquid to the tip of the bur and flushing liquid to the jet, or flushing liquid to the jet only, thus affording a dentist a range of functions for the several liquids, as well as driving air and air directed against one face of the diaphragm of the rotary liquid transmission coupling.

Still another object of the invention is also to provide additional liquid volume control valves of manually-operable nature respectively in the lines for the cooling liquid and also the flushing liquid directed to the external jet on the head of the handpiece.

One further object of the invention is to provide a thin elastic sleeve on the interior of the tubular shaft of the turbine and also provide a tightening nut acting against said sleeve to effectively secure the bur within the sleeve and longitudinal passage in the shaft of the turbine to prevent relative rotation between the shank of the bur and said shaft of the turbine, there also being a sealing-type gasket within the inner end portion of the tubular shaft between the rotary seal member and the inner end of the shank of the bur further to prevent any escape of liquid into the interior of the head of the handpiece which contains the rotating turbine and especially the bearings therefor. Details of the foregoing objects and of the invention, as well as other objects thereof, are set forth in the following specification and illustrated in the accompanying drawings comprising a part thereof.

DETAILED DESCRIPTION OF THE PREFERRED EMBODIMENT OF THE INVENTION

Figure 1:
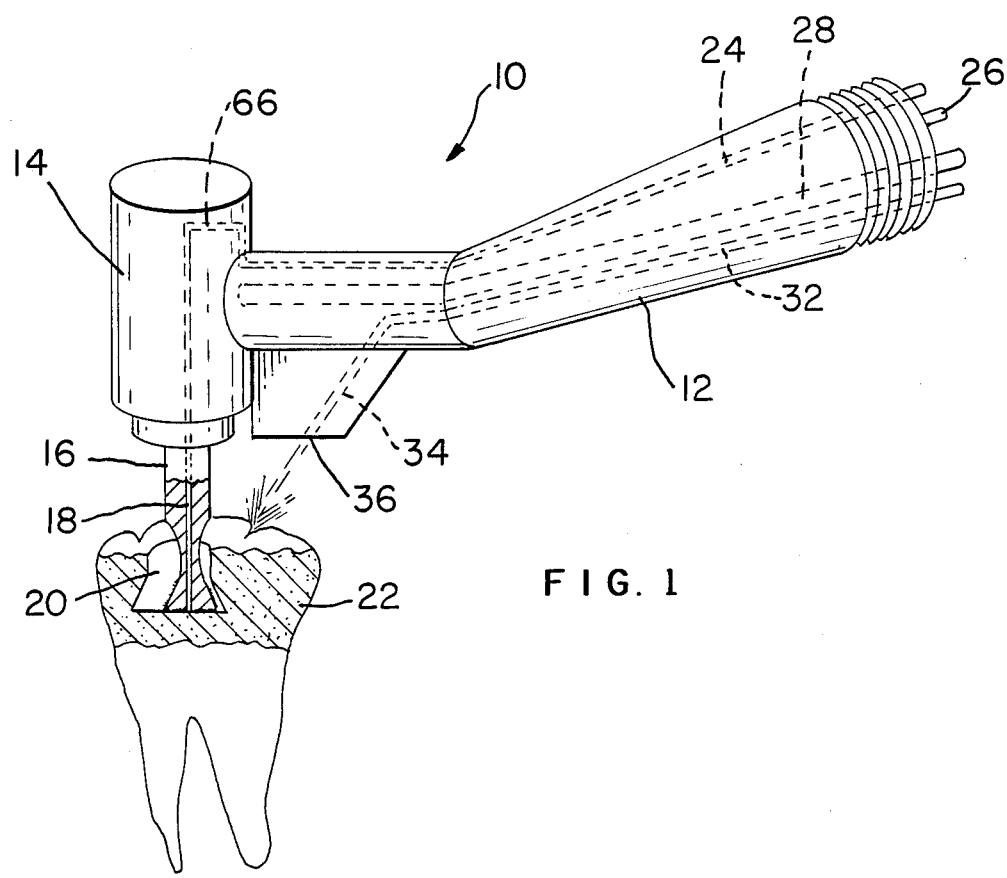
FIG. 1 is a side elevation of a dental handpiece embodying the principles of the present invention and being illustrated in process of preparing a cavity within a tooth, a portion of the tooth being shown in section, to illustrate details of the tip of the bur and said view illustrating in phantom certain passages for liquid and air extending longitudinally through the handle and communicating with the interior of the head of the handpiece.
Figure 3:
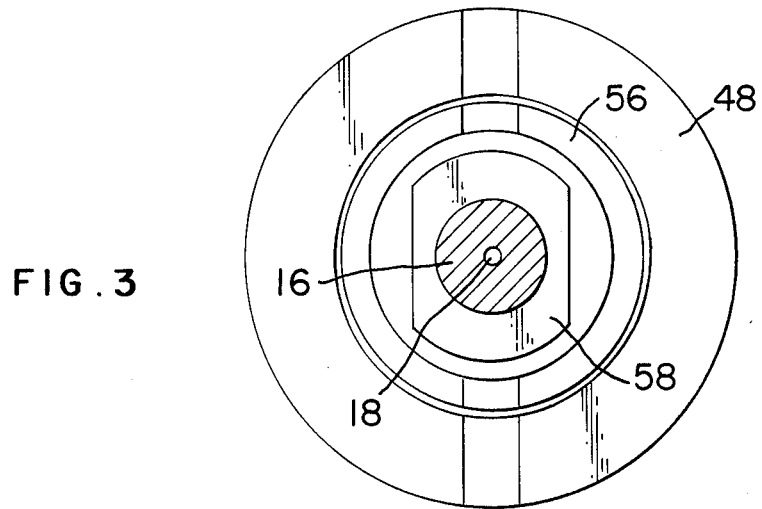
FIG. 3 is an enlarged transverse sectional view as seen on the line 3—3 of FIG. 2.

The present invention primarily relates to a dental handpiece and control mechanism therefor in which a continuous flow of cooling liquid is discharged through the longitudinal opening in the bur for discharge at the outer end thereof into the preparation formed in a tooth by said handpiece and bur at the innerface between the tooth substance and the bur where heat is generated under normal operations and laboratory measurements have disclosed that a bur when rotating at relatively high speed develops 5.88 BTU/min., which must be removed to prevent heat buildup. To evaluate the cooling effect of the invention, a dental drilling analyzer was developed to simulate and maintain reproducible tooth drilling conditions by so-called hollow dental burs through which cooling liquid is discharged.

DRILLING CONDITIONS

Bur speed: 170,000 rpm
Bur torgue: 0.001655 foot lbs.
Bur tooth interface temperature without water after a thirty second running time: 480° F.
Bur tooth interface temperature:continuous 86° F. using a flow rate of 1 CC/min. of 68° F. cooling water.

From these data it shows that the method of utilizing cooling liquid in the present invention definitely prevents heat buildup in the operation of a dental bur. It reduces the water volume 16 times over the state of the art cooling methods and this improvement affords better operating visibility and higher drilling rates without pain to the patient and fear of tooth damage by the dentist.

Because of the reduction of the amount of cooling liquid which is employed, flooding of the operating site is reduced, or eliminated, because the small amount of cooling water leaving the tip of the bur is vaporized by the centrifugal force thereof, and does not appear as liquid water in the highly turbulent area around the cutting bur, thus producing a substantially dry operating area with excellent visibility for the dentist and provides a major improvement over the present state of the art with respect to cooling methods for a dental bur.

The control mechanism, which is described in detail hereinafter, allows the uninterrupted metered flow of cooling liquid, such as water, from the control cabinet through a rotary liquid seal in the handpiece and then to and through the longitudinal opening through the bur and out the tip end of the bur. As might be expected, the rotary seal development employs relatively new technology which affords a substantially leak-proof operation at speeds exceeding 400,000 rpm, with essentially zero drag in a space less than 0.340 inches diameter and 0.050 inches deep. The seal consists essentially of a rotary face and a mating static face in the form of a flexible diaphragm with a 0.015 inches diameter hole in its center.

Some of the materials which are suitable for the elements of the seal comprise, in the rotor: 308 stainless steel, yellow brass, graphite copper and carbon.

In the diaphragm: 0.005 inches thick Mylar, 0.005 inches thick Nylon, 0.010 inches thick ceramic and 0.005 inches thick Beryllium Copper. The selection of the materials depends essentially on the operating speed and the minerals present in the cooling liquid, such as water.

Figure 2:
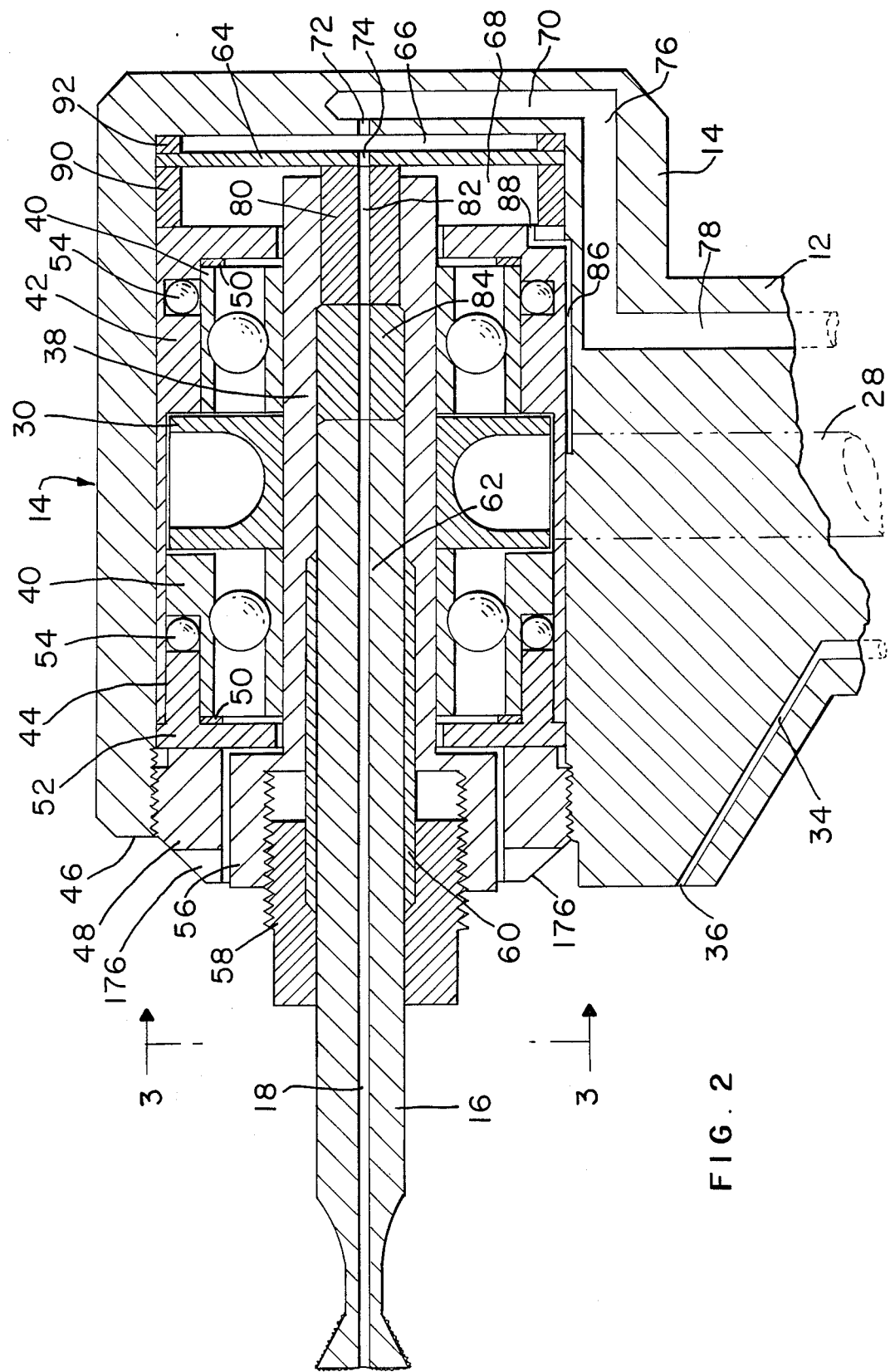
FIG. 2 is a fragmentary, cross-sectional view taken axially through the head of the handpiece and a portion of the handle secured thereto and illustrating details of the interior of the head and especially the manner in which several kinds of liquid are conducted through the head for cooling, as well as flushing purposes, and also showing passages for air to drive the turbine, as well as functioning in relation to a rotary liquid transmission coupling comprising a principal feature of the present invention.

Referring now particularly to FIG. 1 and FIG. 2 of the drawings, there is illustrated a dental handpiece 10, which includes a handle 12 and a head 14, the axis of which is transverse to the handle. Extending from the lower end of the head 14 is a dental bur 16 through which a longitudinal passage 18 extends between opposite ends thereof, as best shown in FIG. 2. As shown in FIG. 1, the tip end of the bur has cutting means which are shown in an exemplary cavity 20 in a tooth 22 in which the cavity is being shaped to receive a filling. The tooth 22 and cavity 20 are merely exemplary, as well as the bur 16.

The handle 12 contains a number of longitudinal passages which are shown in phantom in FIG. 1, these comprising a passage 24, through which cooling liquid is furnished for discharge from the longitudinal passage 18 of the bur. Also, the outermost end of the passage 26, shown in FIG. 1, is exemplary of exhaust means for driving air for the turbine which rotates within the head 14, as shown in FIG. 2. A passage 28 is the means by which driving air, under pressure, is delivered to the head of the handpiece to operate the turbine 30, which is shown in detail in FIG. 2. Lastly, still another passage 32 receives flushing liquid at its outer end and directs the same through an interior angular passage 34, see FIG. 1, through which flushing liquid is discharged from nozzle opening 36 toward the outer end of the bur 16 for purposes of flushing debris resulting from the drilling operation of the bur and this also affords limited cooling of the tooth but for reasons described hereinafter, such cooling is extremely limited and in accordance with the present invention, the principal cooling of the drilling operation is afforded by the longitudinal passage 18 within the bur 16.

The turbine 30 is mounted by a press fit or otherwise upon a tubular shaft 38 upon which the inner races of a pair of antifriction bearings 40 are mounted respectively on opposite sides of the turbine 30. The outerraces of the bearings are mounted within a tubular shell 42, which comprises a housing comprising a cartridge within which the bearings and turbine are positioned for movement as a unit within a bore 44, see FIG. 2, of uniform diameter within the head 14. Especially from FIG. 2, it will be seen that the head 14 is somewhat cup-shaped and has an open outer end 46 which is closed by a threaded closure nut 48. Pre-load washers 50 abut the outer ends of the outer races of the bearings 40 which respectively abut the inner end of the tubular shell 42 and a closure member 52 for said shell, all of which are shown best in FIG. 2. O-rings 54 also aid in positioning the outer races of the bearings with respect to the tubular shell 42.

The tubular shaft 38, at its outer end, has an enlarged portion 56 which is interiorly threaded to receive a tightening nut 58 which engages one end of a thin compressible tube 60, the major portion of which is disposed within the tubular shaft 38 and receives the shank 62 of the bur 16, the compressible tube 60 receiving a substantial length of the shank 62 and, when the tightening nut 58 is tightened, the shaft of the bur is securely clamped to the tubular shaft 38, whereby no relative rotation exists between the bur and the shaft.

One of the outstanding improvements afforded by the present invention comprises a rotary liquid transmission coupling, the primary elements of which comprise a flexible diaphragm 64, the principal preferred materials from which the same may be made being set forth above. The diaphragm 64 is mounted intermediately between a relatively flat space 66 in the inner end of the head 14 and annular space 68 into which the innermost end of the shaft 38 extends, as clearly shown in FIG. 2. The head 14 also includes a radial passage 70, which is plugged at the outer end thereof and the inner end extends past the axis of the head and a central opening 72 of small diameter forms communication between passage 70 and space 66 for the passage of cooling liquid to space 66. Diaphragm 64 also has a small central opening 74, which is coaxial with opening 72. Cooling liquid is furnished to radial passage 70 by means of connecting passages 76 and 78, passage 78 actually comprising the inner end of passage 24 by which cooling liquid is furnished to the head 14.

The rotary liquid transmission coupling also comprises a rotary seal member 80, which preferably is formed from solid carbon which has good lubricating characteristics, especially when used in contact with the diaphragm 64 when formed from self lubricating plastic, such as Mylar or Nylon. The member 80 also has a central passage 82 which is coaxial with openings 72 and 74 and serves to communicate with the longitudinal passage 18 in the bur 16. In the preferred construction of the invention, a gasket 84 is positioned between the innermost end of the shank 62 of bur 16 and one end of the rotary seal member 80. Gasket 84 also has a central passage coaxial with passage 18 of the bur 16 and passage 82 of the seal member 80. The operation of the rotary liquid transmission coupling also is dependent upon the delivery of a limited amount of the driving air which is furnished from passage 28 in the handle 12 of the handpiece to a bypass conduit 86 of small size, which exits at 88 in the annular space 68 for the following purpose:

The operation of the rotary liquid transmission coupling is as follows: Back pressure is effected by cooling liquid within the flat space 66, as received from radial passage 70 through opening 72 and is exerted against a right-hand surface of diaphragm 64, as viewed in FIG. 2, while air under controlled pressure is furnished to annual space 68 and exerts pressure against the surface of the diaphragm next to space 68. The air and liquid pressures preferably are regulated so as to exert equal pressure against opposite surfaces of the diaphragm 64 and thereby maintain the end of seal member 80 in close contact with the adjacent surface of the diaphragm 64. This is especially desirable upon start-up of the turbine so that frictional contact will not cause overheating between the relative static and rotating surfaces of the diaphragm and seal member, and when steady operation of the turbine occurs at high speeds, no appreciable friction will be generated and the temperature of the cooling liquid likewise is present to effect the cooling of the two relatively movable members.

The diaphragm 64 is mounted between suitable annular gaskets 90 and 92, which, for example, may readily be formed from silicone rubber and thereby secure the edges of the diaphragm in sealed manner within the head of the handpiece.

CONTROL SYSTEM FOR AIR AND LIQUIDS

Figure 4:
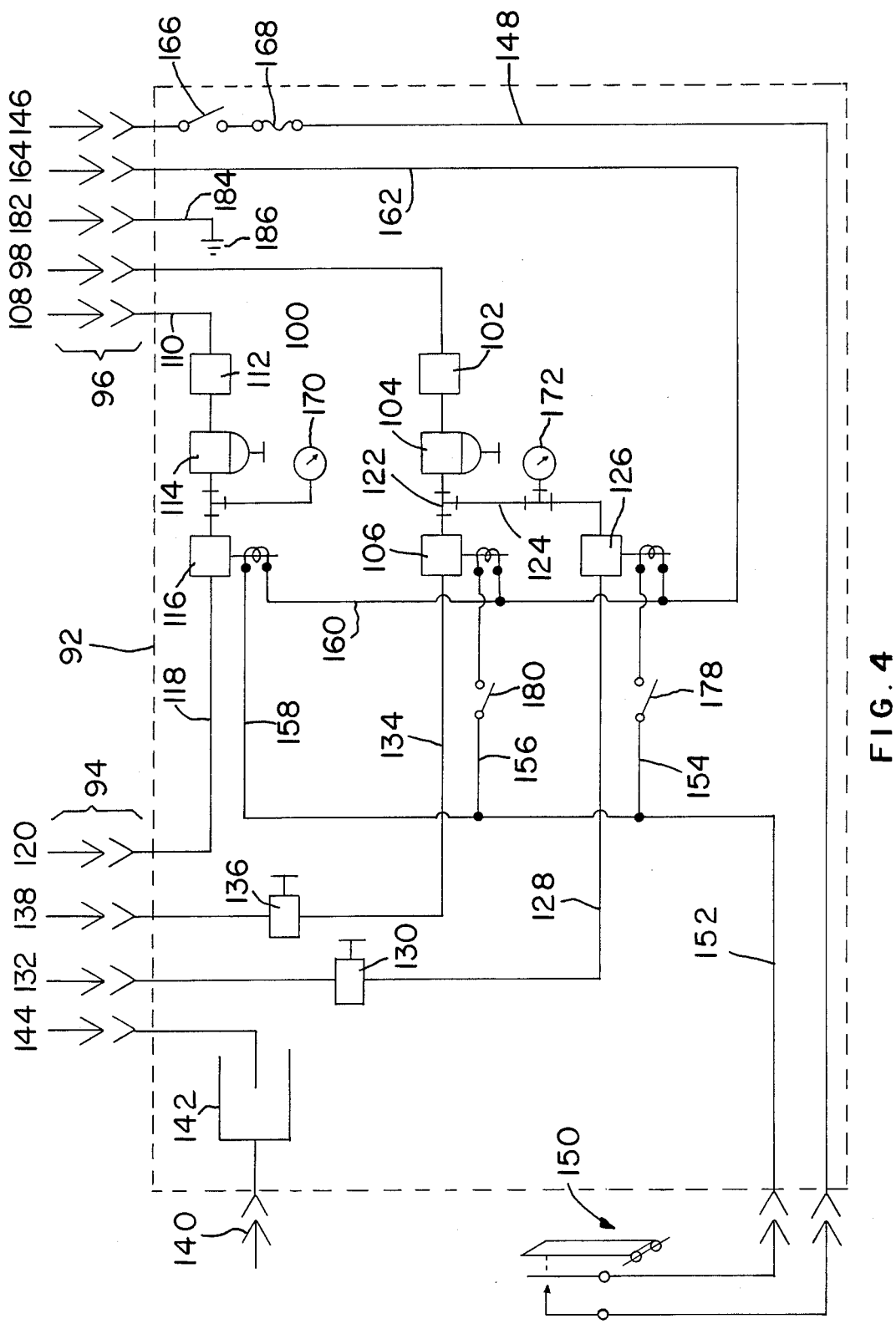
FIG. 4 is a diagrammatic illustration of control mechanism by which several types of liquid under controlled pressures as well as air under controlled pressure, are delivered to the head of the handpiece.

The control mechanism by which driving air is applied to the turbine in the head of the handpiece and cooling liquid, as well as flushing liquid, are regulated as to volume and pressure for delivery to the head of the handpiece, is best shown schematically and diagrammatically in FIG. 4, it being understood the entire control unit is mounted in a small cabinet 92, illustrated by dotted lines in FIG. 4. The plug and socket units 94 and 96 are illustrated diagrammatically by spaced V's, and it will be understood that various air and liquid conducting tubes, as well as electric circuits, will be contained within cables, not shown, as currently used in many types of dental equipment at present. For example, the plug 98 is connected to a source of cooling liquid and passes through conduit 100 to a filter 102, a liquid pressure regulator 104 and then to a liquid control valve 106, which preferably is of the electric solenoid type. Compressed air plug 108 is connected to a suitable source of compressed air and conduit 110 conducts the air to an air filter 112, an air pressure regulator 114 and an air flow control solenoid valve 116. From the valve 116, conduit 118 communicates with plug 120, which connects conduit 118 with plug 120 to which driving air conduit 28 is connected.

Liquid pressure regulator 104 and liquid control valve 106 are connected by conduit 122 to which a bypass conduit 124 is connected to convey flushing water to an electric solenoid valve 126 and from which line 128 extends to water volume metering valve 130, which is manually-settable and communicates with plug 132 that is innerconnected to passage 32 in the handle 12 of the handpiece, by which flushing liquid is delivered to nozzle 36. Solenoid control valve 106 for cooling liquid communicates with line 134 and manually-operable water volume metering valve 136, and is connected to plug 138, which is connected to conduit 24 in the handle of the handpiece for the delivery of cooling liquid to the bur 16.

Exhaust air from the turbine, after driving the same, discharges through passage 26 in the handle of the handpiece and connects to plug 144, shown in FIG. 4, for discharge of the exhausting air to an air-water separator 142, which is connected to outlet plug 140, as seen in FIG. 4.

The electrical system, which essential controls and operates the electric solenoid valves 106, 116 and 126, comprises a plug 146, which is connected to a suitable source of current. It is connected to line 148, which extends to one pole of a foot-actuated switch 150 and the opposite pole of the switch is connected by line 152 to branch lines 154, 156 and 158, which respectively are connected to the solenoids of solenoid valves 106, 116, and 126. The opposite ends of the coils of the solenoids are connected respectively to a common line 160, which is connected to a neutral line 162, which, in turn, is connected to plug 164. Returning to line 148, it will be seen that it includes a main switch 166 and a fuse 168. Also, an air-pressure gauge 170 is connected to the line between air-pressure regulator 114 and air flow control solenoid valve 116 for ready observation. Similarly, water pressure gauge 172 is connected in bypass conduit 124 and suitably visible to an operator of the system.

From the foregoing it will be seen that upon closing the foot switch 150, air pressure rises before the liquid pressure causes the diaphragm 64 to become slightly spaced from the rotary seal 80, and thereby allows a limited amount of air to flow through the bur around the open seal. This prevents dry operation of the seal which, if permitted, could damage it. Air also passes through the opening 74 in the seal and prevents liquid from passing through the open seal. When the liquid pressure equals the air pressure on the opposite sides of the diaphragm, the seal effected by the diaphragm closes or partly closes, allowing a small amount of air to continue to pass to the lower pressure inside the longitudinal opening of the bur. Where it exits at the bur tip, as the mixture of water and air, the amount of air leaking through into the bur reduces the seal friction drag and completely eliminates liquid getting into the ball bearings of the turbine when the drill is running. When the driving air for the turbine is shut off, the seal completely closes because of pressure loss on the rotary mating side of the diaphragm. A conventional cooling liquid jet spray or flush system is provided to allow the use of standard solid shank burs in the handpiece, if desired. A preferable silicone rubber gasket 84 is provided between the rotary seal 80 and the inner end of the shank of the bur and said shank is securely fastened to the rotary shaft 38 by the compression of the compressible sleeve or tube 60, which firmly engages the shank of the bur by tightening the nut 58 which, incidentally, has flats 174 on opposite sides of nut 58. Further, the closure nut 48 for the cartridge has shallow slots 176 formed therein in opposite directions for the reception of an appropriate tool by which the nut 48 can be rotated to suitably install the cartridge in its bore 44 within the head 14.

One of the useful aspects of the present invention also resides in the fact that branch lines 154 and 156 respectively include manually-operable control switches 178 and 180, which are connected in the circuits to the electric solenoid valve 126 and the liquid control valve 106, whereby three modes of cooling are possible. Mode 1 comprises directing cooling liquid to the bur only through plug 138, as controlled by the water volume metering valve 136; Mode 2 comprises supplying cooling liquid to the bur and also flushing liquid to nozzle 36; and Mode 3 comprises directing cooling water only to nozzle 36, the operation of the manual switches 178 and 180 being the means by which such modes are established or discontinued.

It also will be seen that by the various control means for pressure and volume, a delicate balance is established in the pressures exerted against the diaphragm 64 and, when the control means are properly operated, effective sealing is established between the rotatable seal member 80 and the adjacent surface of the diaphragm 64 without undue wear occurring.

The cabinet 92 is made of any suitable material, such as plastic, sheet metal, or otherwise. For purposes of grounding the cabinet, especially if made of metal, as well as all the circuitry therein, a plug 182 is provided, as shown in the upper right-hand corner of FIG. 4, in exemplary manner, and a conductor 184, which is connected to the socket for plug 182, is connected to a ground 186.

The foregoing description illustrates preferred embodiments of the invention. However, concepts employed may, based on such description, be employed in other embodiments without departing from the scope of the invention. Accordingly, the following claims are intended to protect the invention broadly, as well as in the specific forms shown herein.

I claim:

1. An air-turbine dental handpiece comprising in combination,
   a. a handle having passages therein attachable respectively to sources of air and cooling liquid under controllable pressure,
   b. a hollow head connected to one end of said handle and having separated additional passages for air and cooling liquid respectively connected to said passages therefor in said handle,
   c. a turbine rotatably mounted in said head upon bearings at opposite ends of a tubular shaft projecting respectively in opposite directions through said turbine and bearings and said air passage in said head directing air under pressure solely to said turbine to drive it,
   d. a dental bur having a longitudinal opening extending entirely therethrough for the passage of cooling liquid therethrough and insertable operatively and axially within said tubular shaft, the cutting end of said bur projecting beyond one end of said shaft and the opposite end of said shaft terminating adjacent the upper interior portion of said head, and
   e. a rotary liquid transmission coupling mounted within the upper portion of said head and including a member abutting the innermost end of said tubular shaft and provided with a passage aligned with the innermost end of said tubular shaft for transmission of cooling liquid solely to the upper end of said passage in said bur for transmission thereof to the outer end of said bur and operative to seal said passage for cooling liquid in said bur against escape of liquid to said bearings and turbine.

2. The dental handpiece according to claim 1 in which said rotary liquid transmission coupling comprises a flexible diaphragm sealed at the edges thereof in the upper end portion of said head, said cooling liquid passage in said head being arranged to discharge liquid against one face of said diaphragm and said diaphragm having a small substantially central opening coaxial with the upper end of said tubular shaft, and said upper end of said shaft comprising a rotary seal rotatable against the portion of the other face of said diaphragm which is coaxial with the opening therein and said rotary seal has an axial passage coaxial with said opening in said diaphragm, whereby cooling liquid directly under pressure against said one face of said diaphragm biases the same against said rotary seal on said shaft and permits discharge of cooling liquid to and through the axial passage of said bur to the discharge end thereof.

3. The dental handpiece according to claim 2 in which said rotary seal at the upper end of said shaft is an insert press-fitted into the innermost end of the tubular shaft.

4. The dental handpiece according to claim 3 in which said diaphragm comprises thin self-lubricating plastic sheet material and said rotary seal is solid carbon and has said axial passage therein coaxial with the central opening in said diaphragm.

5. The dental handpiece according to claim 3 in which the innermost end of said tubular shaft operates in an annular space in the upper end of said head and across which said diaphragm extends and additional passage for air in said head communicates with said annular space and directs air against the lower face of said diaphragm initially upon start-up of the turbine to minimize friction between said rotary seal and said diaphragm until cooling liquid commences to discharge through the opening in said diaphragm and passage in said rotary seal to said bur passage.

6. The dental handpiece according to claim 5 further including control means in conduits connected between the passages in said handle for air and cooling liquid and sources thereof under pressure and operable to control the pressure thereof as applied against the opposite surfaces of said diaphragm to maintain said diaphragm in contact with said rotary seal at all times while the turbine is operating.

7. The dental handpiece according to claim 6 further including a supplemental conduit in said handle of the handpiece connected to a source of flushing liquid under pressure and said handpiece having a nozzle extending from said handle adjacent said bur and directed toward said bur to flush debris from a dental preparation formed by said bur.

8. The dental handpiece according to claim 7 further including a solenoid valve in a conduit for flushing liquid connected to a first switch in a source of current and said cooling liquid for said bur also being delivered from a source of such liquid through a conduit connected to the handle of said handpiece, another solenoid valve in said latter conduit and connected to a source of current through a second switch, said switches being selectively operable to deliver only cooling liquid or flushing liquid to said handpiece or to deliver both cooling and flushing liquid thereto.

9. The dental handpiece according to claim 6 in which said control means comprises pressure regulators manually-adjustable in respective supply lines for air and also for the cooling and flushing liquids.

10. The dental handpiece in accordance with claim 1 in which said rotary liquid transmission coupling comprises a pressure-operated diaphragm stationarily mounted in the innermost end of said head and rotatably engaged sealably by a seal member fixedly mounted in the innermost end of said tubular shaft.

11. The dental handpiece in accordance with claim 10 in which said diaphragm is formed of self-lubricating plastic sheet material.

12. The dental handpiece according to claim 11 in which said seal member in the innermost end of said tubular shaft also has lubricating characteristics.

13. The dental handpiece according to claim 11 in which said cooling liquid as delivered to the innermost end of the passage in said bur also causes pressure against said diaphragm.

14. An air-turbine type dental handpiece having a head on the outer end of a handle and a bur provided with an axial passage therethrough to transmit cooling liquid to the outer end of said bur, said turbine being mounted on a tubular shaft between bearings spaced from opposite ends of said shaft which receives said bur axially, liquid passage means in said handle connectable to a source of cooling liquid, a rotary liquid coupling in the upper portion of said head communicating with said passage means in said handle and operable to seal the turbine from contact by said cooling liquid while moving through said coupling to and through said axial passage in said bur, in combination with a control system communicating with a source of cooling liquid and including conduit means extending from a source of liquid successively to: a liquid filter, a pressure regulator, and a solenoid valve connected to a source of current and a foot-operated switch operable when closed to open said valve and deliver cooling liquid to a volume regulating metering valve and then to said handpiece.

15. The dental handpiece according to claim 14 further including another axial passage in said handle to transmit air under pressure to said head adjacent said turbine to drive the same and said passage for air in said handle being connected to an additional control system connectable to a source of air under pressure and including in series: an air filter, air pressure regulator, a pressure gauge and a solenoid valve connectable to a source of current by a line connected to said foot-operated switch operable to activate said valve and permit driving air to be delivered to said turbine to operate at a speed controlled by said air pressure regulator.

16. The dental handpiece according to claim 15 further including a small takeoff passage in said head communicating with said axial passage in said handle and receiving a small portion of said driving air therefrom and said head having a circular space therein extending around the innermost end of a tubular shaft on which said turbine is mounted between bearings spaced from the opposite ends of said turbine, said takeoff air passage communicating with said circular space and operable to exert limited pressure against one face of a diaphragm of said rotary liquid coupling while cooling liquid exerts pressure against the other face of said diaphragm in a manner to maintain said diaphragm against upper end means of said tubular shaft and thereby prevent leakage of cooling liquid to said bearings for said turbine, and said diaphragm having a central opening communicating with the innermost end of said tubular shaft to transmit cooling liquid to the outer end of said bur.

17. The dental handpiece according to claim 14 further including a flushing nozzle on said handle directed toward the outer end of said bur and said handle including still another axial passage connected at one end to said flushing nozzle, the opposite end of said axial passage being connected in series to: a liquid volume control valve, a solenoid valve connectable to a source of current through a control switch in circuit with said aforementioned foot-operated switch and operable to direct flushing liquid to said nozzle when said control switch and foot-operated switch are closed.

18. The dental handpiece according to claim 14 in which said rotary liquid coupling comprises a disc of limited flexibility having a central opening and sealed at the edges thereof between a thin space in the upper portion of said head and a short annular space into which the innermost end of said tubular shaft extends into contact with said diaphragm coaxially with said opening therein.

19. The dental handpiece according to claim 18 in which said innermost end of said tubular shaft has a short rotary seal member of solid carbon mounted closely fitted therein and having an axial passage therethrough coaxial with the longitudinal opening in said bur and said central opening in said diaphragm, said seal member rotatably abutting one surface of said diaphragm.

20. The dental handpiece according to claim 14 further including a thin tubular compression sleeve coaxially within the interior of said tubular shaft and engageable with a midportion of the shank of said bur and operable to frictionally engage said shank to prevent relative rotation between said bur and shaft, and a tightening nut threadable into the outer end of said shaft and engaging a portion of said sleeve to tighten the same into firm engagement with the shank of said bur.

* * * * *